United States Patent [19]

Fymat

[11] 4,329,053
[45] May 11, 1982

[54] FREQUENCY-SCANNING PARTICLE SIZE SPECTROMETER

[76] Inventor: James C. Fletcher, Administrator of the National Aeronautics and Space Administration, with respect to an invention of, Salt Lake City, Utah Alain L. Fymat, Pasadena, Calif.

[21] Appl. No.: 65,676

[22] Filed: Aug. 10, 1979

Related U.S. Application Data

[63] Continuation of Ser. No. 553,210, Feb. 26, 1975, abandoned.

[51] Int. Cl.³ .............................................. G01N 15/02
[52] U.S. Cl. .................................... 356/336; 356/338
[58] Field of Search ................. 356/338, 336; 250/574

[56] References Cited

U.S. PATENT DOCUMENTS 2,788,702  4/1957  Baum, Jr. ............................ 356/340
3,724,951  4/1973  Seelbinder ........................... 356/336

*Primary Examiner*—Vincent P. McGraw
*Assistant Examiner*—Matthew W. Koren
*Attorney, Agent, or Firm*—Paul F. McCaul; John R. Manning

[57] ABSTRACT

A particle size spectrometer having a fixed field of view within the forward light scattering cone at an angle $\theta_s$ between approximately 100 and 200 minutes of arc (preferably at 150 minutes), a spectral range extending approximately from 0.2 to 4.0 inverse micrometers ($\mu m^{-1}$), and a spectral resolution between about 0.1 and 0.2 $\mu m^{-1}$ (preferably toward the lower end of this range of spectral resolution), is employed to determine the distribution of particle sizes, independently of the chemical composition of the particles, from measurements of incident light, $I_o$, at each frequency, $\sigma (=1/\lambda)$, and scattered light, $I(\sigma)$, according to the equation:

$$n(r) = -\frac{\beta}{2\pi r^2} \int_0^\infty J_1(y) Y_1(y) y \frac{d}{d\sigma}(\sigma I_\sigma) d\sigma, y = l r \sigma,$$

where $l=2\pi\sin\theta$, $\theta$ being the fixed viewing angle $\theta_s$ at which scattered light is measured, r is particle size, $\sigma$ is the reciprocal of wavelength, $J_1$ is a Bessel function of first kind and order unity, $Y_1$ is a Bessel function of second kind and order unity. The quantity, $I_\sigma$, is the ratio of scattered light to incident light at each frequency interval. The apparatus is a passive remote sensor that can be used in laboratories, field stations, flying aircrafts and airships, and on board an orbiting satellite.

10 Claims, 4 Drawing Figures

4,329,053

FREQUENCY-SCANNING PARTICLE SIZE SPECTROMETER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

This is a continuation, of application Ser. No. 553,210 filed Feb. 26, 1975, now abandoned.

BACKGROUND OF THE INVENTION

This invention relates to a method and apparatus for determining the distribution of particle sizes of a scattering medium of unknown chemical composition. The medium may consist of a composite mixture of arbitrary numbers of chemically different particles embedded in various gases.

There is a continuing need to determine the size distribution of any arbitrary number of particle species which may present a distribution in their refractive indices, and which may be embedded in a scattering medium of unknown chemical composition, for such industrial purposes as environmental pollution monitoring and control, chemical analyses, aeronautical engineering and rocket engineering as well as for such other purposes as meteorological research, geophysical research, and biomedical analyses. The composite mixture of particles and gases may be contained in an experimental chamber, suspended freely in the air, or suspended in fluids such as medical plasmas, or in any other similar situation where particulate sizes must be determined without disturbing the sample.

Conventional direct sampling methods where particles are thermally precipitated, impacted or otherwise mechanically collected, as well as in situ imaging methods, present several problems. Some of these problems are: disturbing of sample, low sampling rate, discontinuous sampling, collection efficiency problems, long sampling time and painstaking analyses. Additionally, they cannot be used as remote sensors for realtime operation.

To avoid these problems of direct sampling, and at the same time provide a remote sensing capability, methods have been developed which exploit the forward light scattering properties of particles at frequencies within the range 0.198 to 4.070 inverse micrometers ($\mu m^{-1}$) or within any larger range extending down to 0.02 $\mu m^1$ and up to 9.27 $\mu m^{-1}$. Incident light, $I_o$, possessing a spectrum of frequencies in the ranges above specified, is characterized ony by its wavenumber, $\sigma_i$, the reciprocal of the wavelength, $\lambda_i$. Its direction of propagation, $\theta_i$, is the direction of reference, $\theta_i=0$. The subscript, i, here stands for "incidence." Particles are characterized by their nature and micro-structure, respectively represented by a refractive index, m, a complex number, and a size distribution, n (r), representing a partial concentration per unit volume and per unit increment of the radius r. Only n (r) is independent of the wavenumber. The various particles, assumed to be spherical in shape, may also present a distribution in m itself. Gases will be similarly characterized by their number density, i.e. number of atoms or molecules per unit volume, refractive index and geometrical shape. Scattered light, on the other hand, is characterized by its wavenumber, $\sigma_s$, and direction, $\theta_s$, of propagation. Here the subscript, s, stands for "scattering." The direction, $\theta_s$, is thus the scattering angle with reference to the incident light direction $\theta_i$.

For a given incident light, i.e., for a situation where $\sigma_i$ and $\theta_i$ are given, and for a given assembly of scatterers, i.e., for an assembly of particles of given refractive indices, $m(\nu_s)$, and size distribution, n (r), Mie's theory of scattering by a conducting sphere enables us to determine the scattered light for any arbitrary $\sigma_s$ and $\theta_s$. Conversely if the incident light is known for any $\sigma_i$ and $\theta_i$ to be prescribed, and the scattered light is measured for various $\sigma_s$ and $\theta_s$ to be also prescribed, we should be able in principle to infer the properties of the particles, that is their size distribution, and refractive index values at the various $\sigma_s$. In other words, Mie's theory enables us to compute the output, $I_s$, in all its detailed variations if we know the input, $I_o$, and the properties of the particles $m(\sigma_s)$ and $n(r)$. However, what is of interest is a determination of the scatterers from a knowledge of the input, $I_o$, and the output, $I_s$. But from an inversion of Mie's theory it would be possible to determine only the combined relation between the refractive indices, $m(\sigma_s)$, and size distribution, $n(r)$, and not the size distribution separately.

It has been discovered that the Fraunhofer theory of angular diffraction of light of fixed single frequency at an aperture in a plane screen can be extended to a range of multiple frequencies. Under these conditions, the light scattered by a particle is essentially independent of the refractive index, $m(\sigma_s)$, and depends only on its size as though the particle were an aperture in a screen of the same radius. It has also been discovered that, working within the restricted domain of applicability of the theory thus extended ($\theta_s$ between 100 and 200 minutes of arc, approximately, preferably $\theta_s=150$ minutes; and 0.2 $\mu m^{-1} \leq \sigma_s \leq 4.0$ $\mu m^{-1}$, approximately), it is possible to determine size distribution, n (r), independently of refractive indices $m(\sigma_s)$, i.e., to determine size distribution of particles of radius larger than approximately one micrometer ($\mu m$) without knowing anything of their refractive indices, from known incident light, $I_o$, and measured scattered light, $I_s$.

If the assembly of scatterers under study consists of particles of j different species and k different gases, the identical determination of n (r) can still be made provided only j, k, and the so-called depolarization factor of each gas (this is defined as the ratio of scattered intensities in directions parallel and perpendicular to the plane of scattering for an incident beam of natural light), $p_k$, are known.

SUMMARY OF THE INVENTION

In accordance with the present invention, a natural or artificial light source is passed through a volume of scattering particles the size distribution of which is to be determined. The intensity of light scattered by the particles, at a fixed angle between approximately 100 and 200 minutes of arc from the direction of incident light, preferably 150 minutes of arc, is recorded as a function of frequency, $I(\sigma)$. Records are made across the approximate frequency interval 0.20 $\mu m^{-1}$ to 4.0 $\mu m^{-1}$, at frequency steps smaller than about 0.2 $\mu m^{-1}$. Simultaneously, the intensity of the incident light at each frequency, $I_o$, is recorded. The ratio $I_\sigma$ of scattered light, $I(\sigma)$, to incident light, $I_o$, is then obtained. In order to determine the size distribution, n (r), from the ratio $I_\sigma$, the following equation has been derived and investigated with regard to its correctness, the uniqueness of the solution obtained from it, and the stability of this solution with regard to inherent experimental and analytical noises:

$$n(r) = -\frac{l^3}{2\pi r^2} \int_0^\infty J_1(y)Y_1(y)y \frac{d}{d\sigma}(\sigma I_\sigma)d\sigma, y = lr\sigma,$$

where $J_1$ is a Bessel function of first kind and order unity, $Y_1$ is a Bessel function of second kind and order unity, $l = 2\pi \sin\theta$, $\theta$ being the fixed viewing angle at which scattered light is measured, $r$ is particle radius, and $\sigma$ is the reciprocal of wavelength. In the case of j particle species embedded in k gas species, the former equation remains valid provided only $I_\sigma$ is changed to the following expression:

$$I_\sigma \longrightarrow G_\sigma = \frac{1}{j}\left[ 4\cos\theta\, I_\sigma - \frac{3}{2}\sum_k \frac{2 - \rho_k \cos 2\theta}{2 + \rho_k}\right],$$

where $\rho_k$ is a so-called depolarization factor of the $k^{th}$ gas defined as the ratio of scattered intensities in directions parallel and perpendicular to the plane of scattering for an incident beam of natural light.

The novel features of the invention are set forth with particularity in the appended claims. The invention will best be understood from the following description when read in conjunction with the accompanying drawings.

BRIEF DESCRIPTION OF THE DRAWINGS

The FIG. 1 illustrates schematically an example of apparatus for the method of the present invention, where the method steps operating on measured quantities are represented by functional blocks.

DESCRIPTION OF THE PREFERRED EMBODIMENTS

Figure 1:
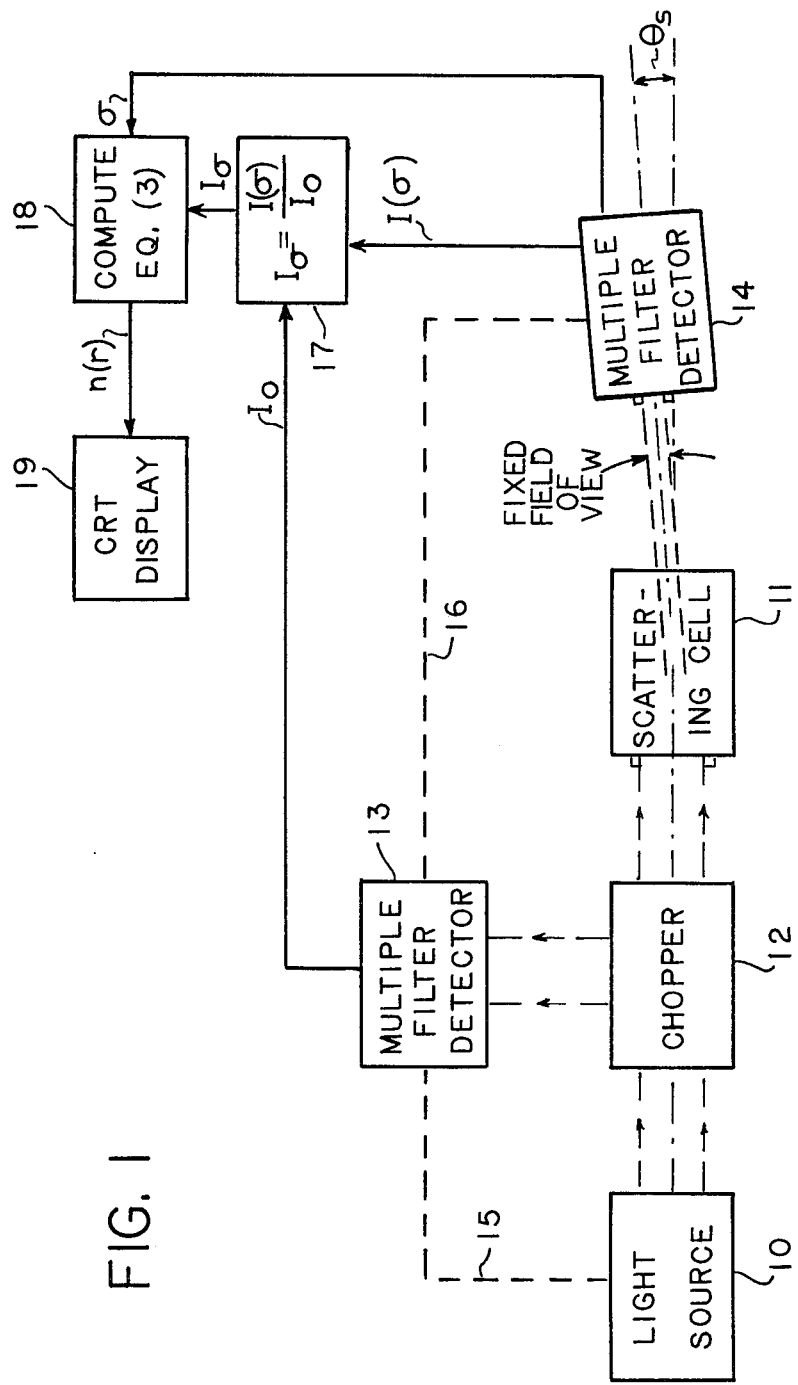

Referring to FIG. 1, a natural or artificial light source 10 is directed to a cell 11 filled with a medium of unknown chemical composition through a chopper 12 which cyclically deflects the incident light, $I_o$, to a reference multiple-filter detector 13 for the purpose of measuring the incident light intensity as the light source is scanned in frequency. The filter of the detector is preferably changed as the light source is scanned in order that the reference measurement $I_o$ be accurate for each frequency of incident light. An object multiple-filter detector 14 is likewise controlled to detect scattered light at the different prescribed frequencies as the source is scanned. That is represented by dotted lines 15 and 16 for synchronized control of the detector and light source. The reference and object multiple-filter detectors can be detector arrays in which each detector element is slaved to a specific frequency.

The object detector 14 is designed to have a fixed field of view at a fixed angle $\theta_s$ of less than 6° within the forward scattering cone of the cell 11. For best results, the scattering angle $\theta_s$ is made about 150 minutes of arc, but it may be any angle between 100 and 200 minutes of arc, approximately. It is also designed to have a spectral resolution, i.e., a frequency step, $\Delta\sigma$, as coarse as 0.2 $\mu m^{-1}$ or as fine as 0.1 $\mu m^{-1}$, and to operate within the approximate spectral frequency limits of $\sigma_{min} = 0.2$ $\mu m^{-1}$ and $\sigma_{max} = 4.0$ $\mu m^{-1}$.

Although a cell is indicated, the scattering particles forming a homogeneous cloud or medium between the light source and the detector may be contained in a laboratory chamber, suspended freely in the air, contained in fluids such as plasmas and blood, emitted from any type of industrial or engine nozzle, or in any other similar situation where particulate sizes must be determined without disturbing the sample in any manner. Also, although a variable light source is indicated, radiance from particles that exhibit significant thermal emission, e.g., radiance from atmospheric particles which emerges from the atmosphere, can also be used. On the other hand, a light source may be employed that emits all of the frequencies to be scanned. In the latter case, the control for frequency scanning may be effected at only the detectors 13 and 14, while in the former case it is effected only at detector 14.

If the foregoing restrictions on the fixed angle, $\theta_s$, spectral frequency range, $\sigma_{min}$ to $\sigma_{max}$, and spectral resolution, $\Delta\sigma$, of the reference and object detectors are observed, the measurements of scattered light $I(\sigma)$ can provide the complete spectrum of particulate sizes, i.e., particle size distribution, $n(r)$, in radii of equivalent spheres, from approximately 1 $\mu m$ to any arbitrarily larger value, including the accurate location of the mode radius (corresponding to the largest concentration of particles). The technique will now be described. Consider an incident beam of radiation of wavenumber, $\sigma = 1/\lambda$, ($\lambda$ = wavelength), and intensity, $I_o$, illuminating a single particle of radius, $r$. The singly-scattered light intensity, $I(\sigma)$, at angle, $\theta$, in units of $I_o$, is expressed by the formula:

$$I_\sigma \equiv \frac{I(\sigma)}{I_o} \approx \left[\frac{r J_1(kr \sin\theta)}{\sin\theta}\right]^2, \theta = \theta_s, \quad (1)$$

where $K = 2\pi\sigma$ and $J_1$ is a Bessel function of first kind and order unity. For a distribution of sizes, $n(r)$, the generalization of this expression will provide the total scattered light intensity:

$$I_\sigma = \frac{1}{\sin^2\theta} \int_0^\infty n(r)r^2 J_1^2(x)dr, x = kr \sin\theta. \quad (2)$$

It may be noted that equations (1) and (2) depend only on r. In order to determine $n(r)$ from measurements of $I_\sigma$, it is necessary to invert this equation. The analytical inverse of equation (2) is obtained in the form:

$$n(r) = -\frac{l^3}{2\pi r^2} \int_0^\infty J_1(y)Y_1(y)y \frac{d}{d\sigma}(\sigma I_\sigma)\, d\sigma, y = lr\sigma, \quad (3)$$

where $l = 2\pi \sin\theta$ and $Y_1$ is a Bessel function of second kind and order unity.

If the scattering medium being illuminated consists of j different species of particles embedded in k different species of gases, equations (2) and (3) remain valid provided only we replace in these equations the quantity $I_\sigma$ by the following quantity:

$$I_\sigma \longrightarrow G_\sigma = \frac{1}{j}\left[4\cos\theta\, I_\sigma - \frac{3}{2}\sum_k \frac{2 - \rho_k \cos 2\theta}{2 + \rho_k}\right], \quad (4)$$

where $\rho_k$ is the depolarization factor of the $k^{th}$ gas.

It must be stressed that Equation (3) utilizing either $I_\sigma$ or $G_\sigma$ is a closed form expression for n(r) which makes no assumption on any analytical form by which this function may be modeled. It is exactly true for the function $I_\sigma$ defined by Equation (2) or the function $G_\sigma$ defined by Equation (4). It may be noted, however, that $\sigma$ will not vary over an infinite range as indicated by Equation (3).

For example, if it is wished to use this instrument as a remote sensor on board a planetary orbiter, $\sigma$ has a lower bound which will vary according to the brightness temperature of the planetary atmosphere of interest. This value of $\sigma$ is that at which the planetary radiation dominates the visible solar radiation reflected by the planet. This is because the thermal radiation from the planet surface and atmosphere system, which is emitted due to the temperature of this surface and atmosphere, is not the absolute zero. Thus, on Earth, this cutoff value is approximately 0.37 $\mu m^{-1}$. However, although the integration indicated in Equation (3) cannot be carried out completely, and it is conceivable that in some extreme cases the distribution n(r) may either not be reproduced exactly or not at all, it has been discovered that an object detector designed to operate within the limits set forth hereinbefore will permit the integration to be carried out to provide the detailed spectrum of sizes (particle size distribution) in equivalent spheres of the scattering particles. These limits provide a unique method which has been submitted to detailed scrutiny as to stability with regard to both inherent experimental and analytical noises.

The first computational step of forming the ratio indicated by Equation (2) is represented by a functional block 17, and the second computational step indicated by Equation (3) is represented by a functional block 18. The ratio can be formed using analog circuits, or upon converting the detector signals to digital form, by digital techniques. In either case, the result of the first computational step is preferably obtained in digital form for storage and subsequent retrieval for solution of Equation (3). The values of this ratio at the several prescribed frequencies are then inserted in Equation (3) which is subsequently solved for various values of r larger than approximately 1 $\mu m$. For example, for $r=r_1$, the equation yields $n_1=n(r=r_1)$; for $r=r_2$, the solution yields $n_2=n(r=r_2)$, and so forth. The set of values $n_1, n_2, \ldots$ is the desired particle distribution n(r). A general purpose computer can be used for solving Equation (3). The computer can be used on a time-sharing basis or a special-purpose computer could be slaved to the apparatus. The output from such a computer is converted to an electrical signal which is then displayed visually on a cathode ray tube (CRT) display 19. Thus, a real-time visualization of the size distribution is provided, such as for the purpose of monitoring the changes in particle sizes that may take place as is the case, for example, with environmental particulate pollution.

Figure 2:
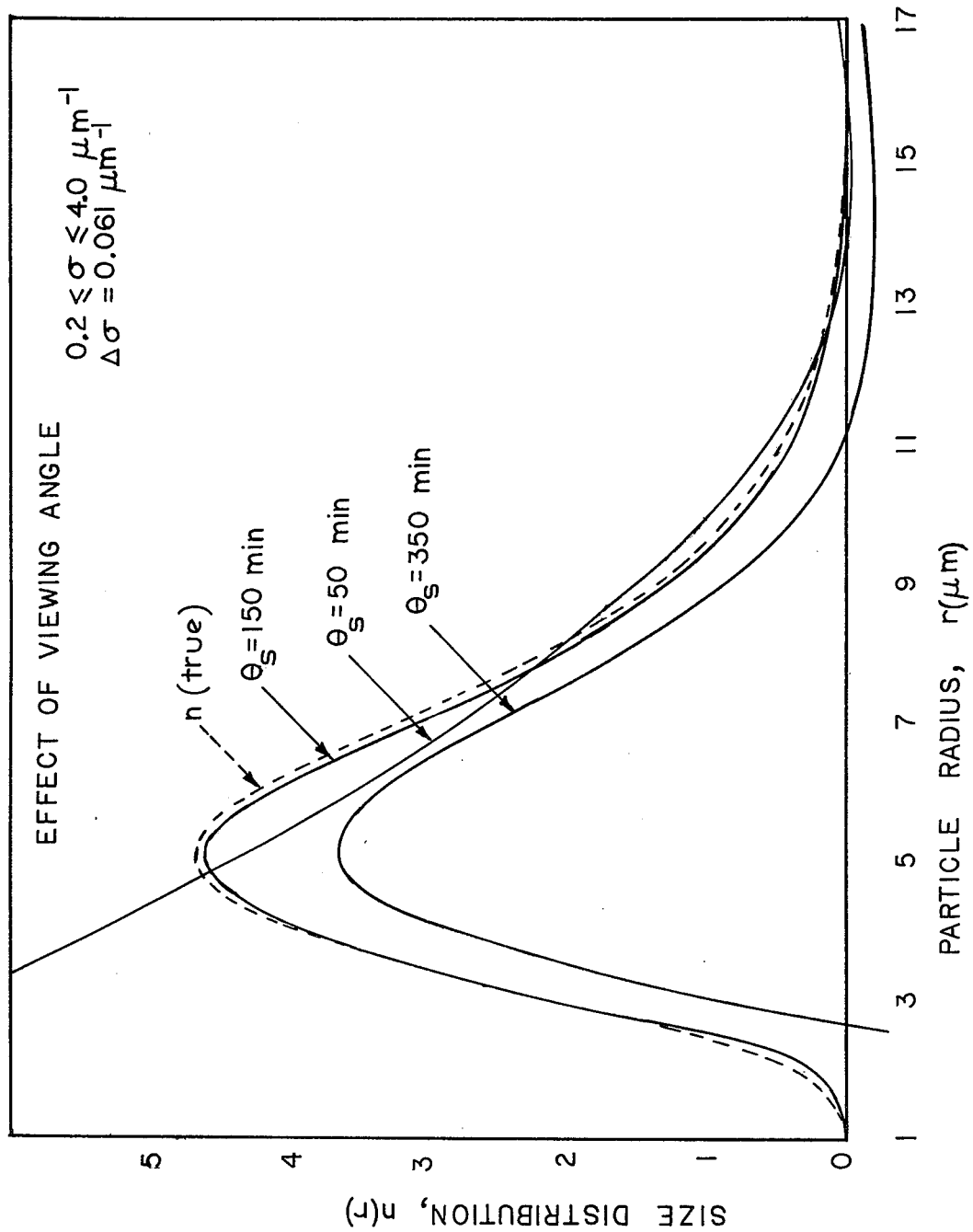
FIG. 2 is a graph showing the effect of viewing angle, $\theta_s$, on determining particle size distribution from light scattered by the particles according to the present invention.

The effect of viewing angle, $\theta_s$, can be appreciated from the graph of FIG. 2 which shows a true plot of particle size distribution by a bell-shaped curved labeled "n(true)" for comparison with particle size distribution curves determined at viewing angles of 50 minutes, 150 minutes and 350 minutes. The distribution curve labeled "$\theta_s=150$ min" is found to be very close to the true distribution curve. Consequently, it is concluded that a viewing angle of about 150 min is optimum. At viewing angles between approximately 100 min and 200 min, the results are still very good, although small negative tails develop close to these two values below 1.5 $\mu m$ radius; but beyond that range there is not only further degradation of the results from the true curve, but totally incorrect results over much of the range of particle sizes. For example, at a viewing angle as small as 50 min, the results indicate a negative distribution between 14 and 17 $\mu m$ radius, and although it seems to follow the true distribution curve as particle radius decreases, it becomes clear at below 8 $\mu m$ radius that the distribution curve is totally in error (meaningless) since size distribution increases, apparently without limit, as the particle radius decreases. Deviation from the optimum viewing angle in the other direction will not produce such absurd results, as shown by the distribution curve labeled "$\theta_s=350$ min". But still the results have so departed from the true distribution as to not be useful except perhaps in locating the peak position. Note the negative distribution above 11 $\mu m$ and below 2.7 $\mu m$ radius. The true distribution cannot, of course, go below zero. This demonstrates the limited range of viewing angles that can be effectively used in this technique.

Figure 3:
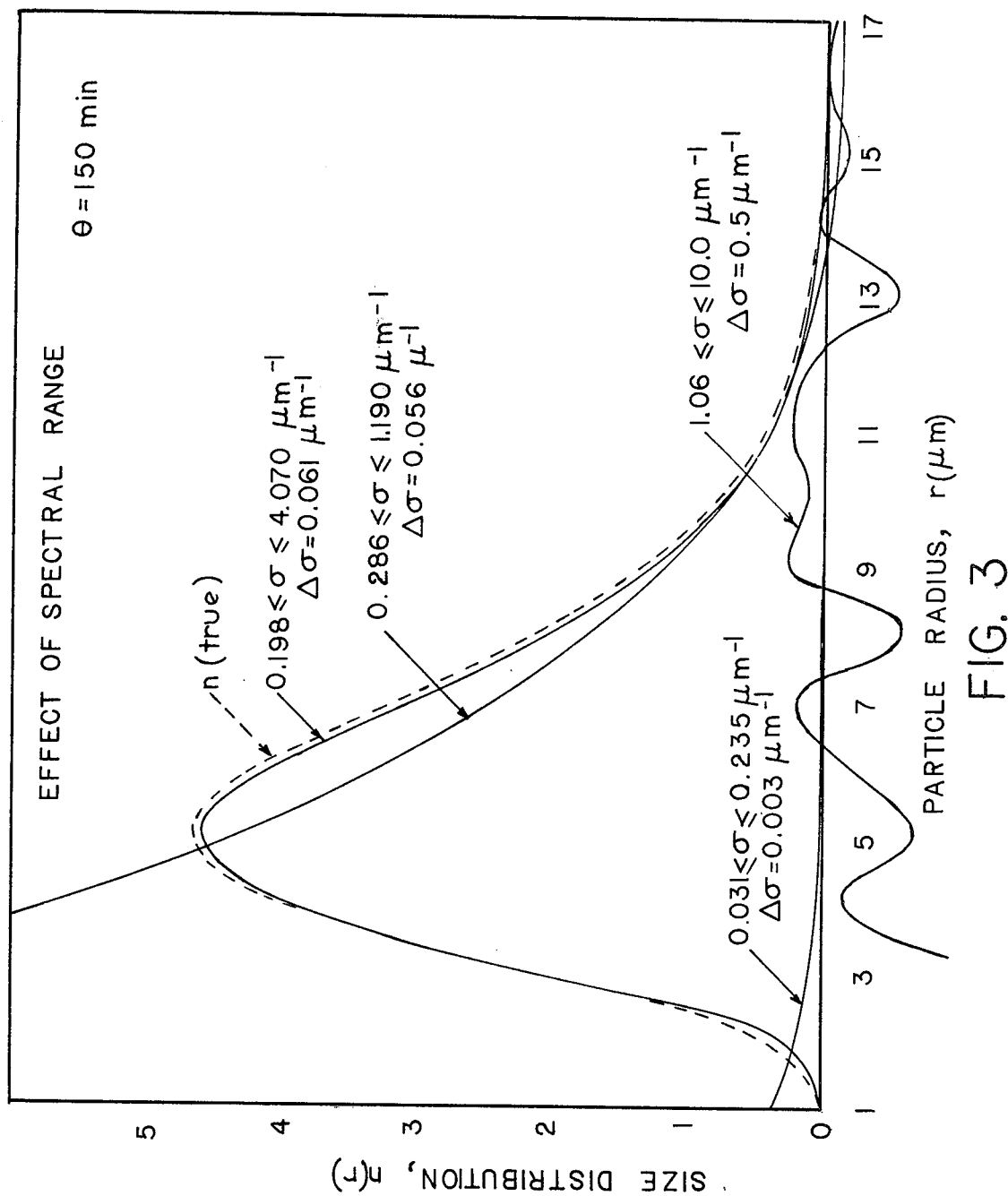
FIG. 3 is a graph showing the effect of spectral range $\theta_{min}$ to $\theta_{max}$, in scanning the frequency of light incident on particles for determining particle size distribution.

The effect of spectral range can be appreciated from the graph of FIG. 3. In the range of about 0.2 to 4.0 $\mu m^{-1}$, the result is very nearly identical to the true distribution curve as shown by a curve labeled "$0.198 \leq \theta \leq 4.070\ \mu m^{-1}$." This result remains substantially the same if the starting value of 0.198 were to be lowered down to 0.02 $\mu m^{-1}$. At the lower part of the range, namely at 0.198 to 2.860 $\mu m^{-1}$, the form of the distribution curve remains about the same but becomes negative at less than 2 $\mu m$ radius. Increasing the upper end of the range to approximately 9.00 $\mu m^{-1}$ produces about the same results, but the distribution curve becomes more negative at less than 2 $\mu m$ radius. Working in a subinterval of the lower part of the optimum range, namely in the range from 0.44 to 2.86 $\mu m^{-1}$, the result is about the same as working at just the lower part of that optimum range, except that the distribution is found to be negative below 3 $\mu m$ radius and above 12 $\mu m$ radius, with decrease of approximately 18% in the peak. Operating at only a narrow central part of the optimum spectral range, namely between about 0.3 to 1.2 $\mu m^{-1}$ produces the absurd result indicated by the curve labeled "$0.286 \leq \nu \leq 1.190\ \mu m^{-1}$." Operating below the optimum range, such as in a range from 0.03 to 0.2 $\mu m^{-1}$ also produces an absurd result, as shown by the curve labeled "$0.031 \leq \sigma \leq 0.235\ \mu m^{-1}$." Lastly, extending the optimum range, for example from 1.0 to 10.0 $\mu m^{-1}$ also produces the absurd result shown by the curve labeled "$1.0 \leq \sigma \leq 10.0\ \mu m^{-1}$."

Figure 4:
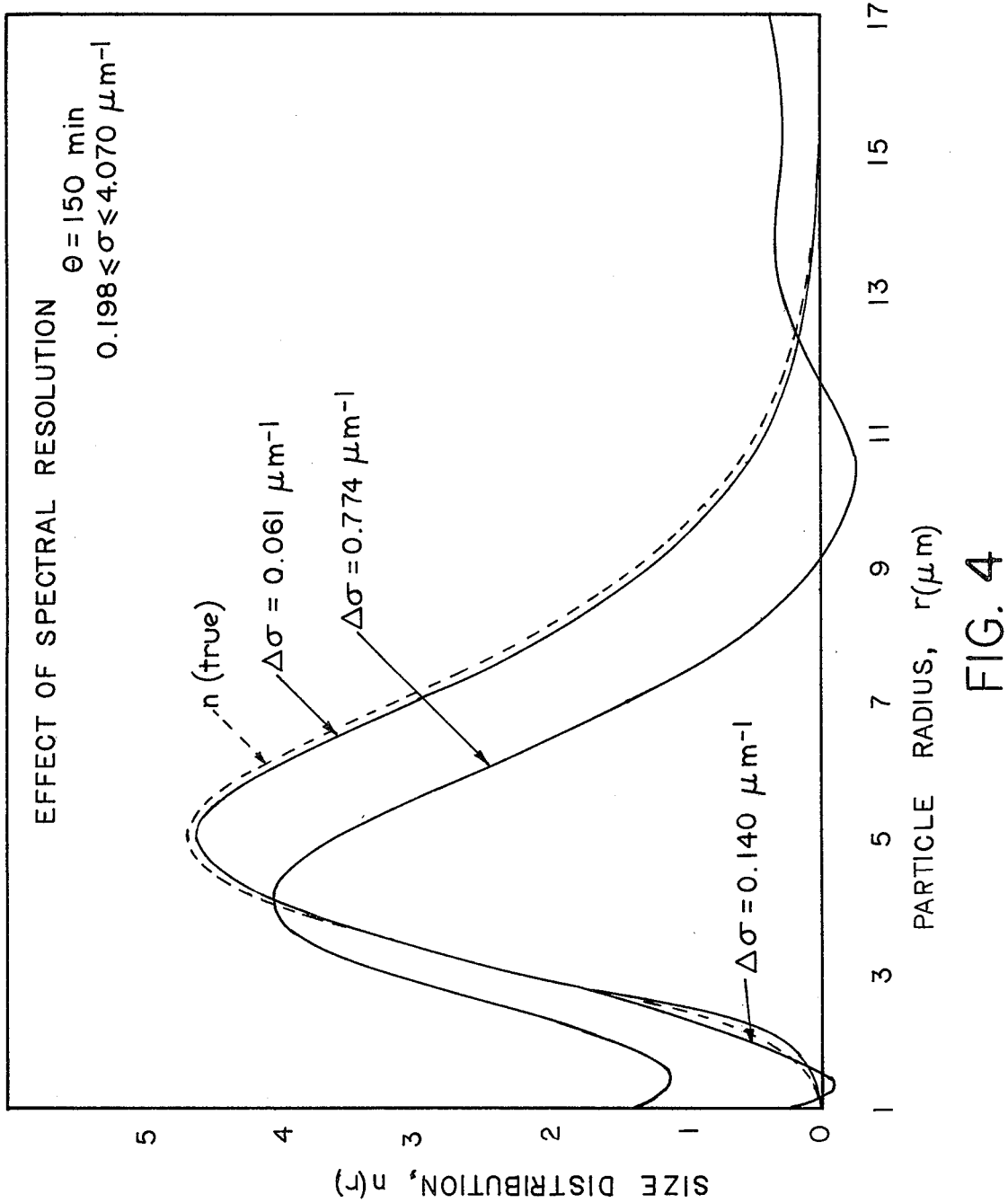
FIG. 4 is a graph showing the effect of spectral resolution, $\Delta\sigma$, in the process of determining particle size distribution according to the present invention.

The effect of spectral resolution is illustrated in FIG. 4. Again the curve labeled n(true) is the theoretical or true particle distribution. The optimum is shown to be a spectral resolution of about 0.06 $\mu m^{-1}$, as shown by the curve labeled "$\Delta\sigma=0.061\ \mu m^{-1}$". However, spectral resolution is less critical than spectral range or viewing angle. A smaller resolution would have no deleterious effect on the result. A larger resolution can be tolerated to about three times the optimum. There, at the resolution of 0.18 $\mu m^{-1}$, the results begin to degrade, and at about 0.80 $\mu m^{-1}$, the results become absurd as shown by the curve labeled "$\Delta\sigma = 0.774$ $\mu m^{-1}$."

The necessary spectral range with the optimum spectral resolution may be achieved by scanning frequency at the detector using a detector-array in which each detector is slaved to a specific frequency, as noted hereinbefore. Alternatively, one or more voltage variable photodetectors are used, and frequency scanning is achieved by varying the bias voltage to the detectors. For most laboratory applications, there will be a specific light source, either variable in frequency or containing all frequencies of interest. In the latter case, scanning the frequencies in the desired range could be accomplished by the use of filters. Such an arrangement would also be used outside the laboratory from a ground-based station such as for determining the size distribution of particles in the Earth's atmosphere, where light from the sun is filtered for scanning the frequency of light passed through a volume of scattering particles. In the case of an orbiting satellite, on the other hand, it is the thermal emission from the atmosphere-surface system that would be filtered.

Although particular embodiments of the invention have been described and illustrated herein, it is recognized that modifications and equivalents may readily occur to those skilled in the art and consequently it is intended that the claims be interpreted to cover such modifications and equivalents.

What is claimed is:

1. A method for producing data values from forward scattered light for determining the size distribution of particles dispersed in a volume of gas independently of the refractive indices of the particles so that their chemical composition need not be known, even with a number of different species of particles dispersed in the volume, and even with a number of different species of gas in the volume, said method comprising the steps of varying the wavelength of light incident on said particles in said volume in incremental steps within a total spectral range of about $0.20 \leq \sigma \leq 4.0$ $\mu m^{-1}$, where $\sigma$ is the wavenumber equal to the reciprocal of wavelength $\lambda$, and the steps over this total range are at intervals of wavenumber, $\Delta\sigma$, of less than about 0.2 $\mu m^{-1}$, and for each interval, producing a signal representative of the wavenumber $\sigma$, for each wavenumber, detecting at a fixed viewing angle the intensity of light forward scattered in a narrow cone by said particles in said volume, said fixed viewing angle being between 100 and 200 minutes of arc from the axis of the scattering cone which coincides with the direction of incident light, and from the intensity, $I(\sigma)$, of scattered light detected, generating a first electrical signal representing the value of intensity of forward scattered light at the narrow angle of detection, for each wavenumber, detecting the intensity, $I_o$, of incident light and generating a second electrical signal representative of the intensity of incident light at the time forward scattered light is detected for the wavenumber, dividing the signal representative of the intensity of forward scattered light, $I(\sigma)$, for each wavenumber by the signal representative of the intensity of incident light, $I_o$, for the same wavenumber to obtain a signal representative of normalized forward scattered light, $I_\sigma$, thereby to provide a set of data for use in determining particle size distribution, $n(r)$, for various values of radius, r, larger than approximately 1 $\mu m$ as a function of the wavenumber $\sigma$ and normalized scattered light, $I_\sigma$.

2. The method as defined in claim 1 wherein said viewing angle is 150 minutes of arc.

3. The method of claim 1 or 2 wherein said spectral range is $0.198 \leq \sigma \leq 4.070$ $\mu m^{-1}$.

4. The method of claim 1 or 2 wherein said incremental steps are at intervals of wavenumber, $\Delta\sigma$, selected to be less than 0.2 $\mu m^{-1}$.

5. A method as defined in claim 1 or 2 wherein said spectral range is $0.198 \leq \sigma 4.070$ $\mu m^{-1}$ and said incremental steps are at intervals of wavenumber, $\Delta\sigma$, selected to be less than 0.2 $\mu m^{-1}$.

6. Apparatus for producing data values from forward scattered light for determining the size distribution of particles dispersed in a volume of gas independently of the refractive indices of the particles so that their chemical composition need not be known, even with a number of different species of particles dispersed in the volume, and even with a number of different species of gas in the volume, said apparatus comprising means for varying the wavelength of light incident on said particles in said volume in incremental steps within a total spectral range of about $0.20 \leq \sigma \leq 4.0$ $\mu m^{-1}$, where $\sigma$ is the wavenumber equal to the reciprocal of wavelength $\lambda$, and the steps over this total range are at intervals of wavenumber, $\Delta\sigma$, of less than about 0.2 $\mu m^{-1}$, and for each interval, producing a signal representative of the wavenumber, $\sigma$, means for detecting at a fixed viewing angle for each wavenumber the intensity of light forward scattered in a narrow cone by said particles in said volume, said fixed viewing angle being between 100 and 200 minutes of arc from the axis of the scattering cone which coincides with the direction of incident light, and from the intensity, $I(\sigma)$, of scattered light detected, generating a first electrical signal representing the value of intensity of forward scattered light at the narrow angle of detection, means for detecting the intensity, $I_o$, of incident light for each wavenumber and generating a second electrical signal representative of the intensity of incident light at the time forward scattered light is detected for the wavenumber.

means for dividing the signal representative of the intensity of forward scattered light, $I(\sigma)$, for each wavenumber by the signal representative of the intensity of incident light, $I_o$, for the same wavenumber to obtain a signal representative of normalized forward scattered light, $I_\sigma$, thereby to provide a set of data for use in determining particle size distribution, $n(r)$, for various values of radius, r, larger than approximately 1 $\mu m$ as a function of the wavenumber, $\sigma$, and normalized scattered light, $I_\sigma$.

7. Apparatus as defined in claim 6 wherein said viewing angle is 150 minutes of arc.

8. Apparatus as defined in claim 6 or 7 wherein said spectral range is $0.198 \leq \sigma \leq 4.070$ $\mu m^{-1}$.

9. Apparatus as defined in claim 6 or 7 wherein said incremental steps are at intervals of wavenumber $\Delta\sigma$ selected to be less than 0.2 $\mu m^{-1}$.

10. Apparatus as defined in claim 6 or 7 wherein said spectral range is $0.198 \leq \sigma 4.070$ $\mu m^{-1}$ and said incremental steps are at intervals of wavenumber, $\Delta\sigma$, selected to be less than 0.2 $\mu m^{-1}$.

* * * * *